(12) United States Patent
Birnkrant et al.

(10) Patent No.: US 11,006,819 B2
(45) Date of Patent: May 18, 2021

(54) FOCUSABLE CAMERA MODULE FOR ENDOSCOPES

(71) Applicant: Karl Storz Endovision, Inc., Charlton, MA (US)

(72) Inventors: Dashiell A. Birnkrant, Worcester, MA (US); Robert Shieh, Uxbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1532 days.

(21) Appl. No.: 14/516,246

(22) Filed: Oct. 16, 2014

(65) Prior Publication Data

US 2016/0106303 A1   Apr. 21, 2016

(51) Int. Cl.
*A61B 1/00* (2006.01)
*A61B 1/05* (2006.01)
*G02B 23/24* (2006.01)

(52) U.S. Cl.
CPC ...... *A61B 1/00188* (2013.01); *A61B 1/00039* (2013.01); *A61B 1/00066* (2013.01); *A61B 1/00096* (2013.01); *A61B 1/051* (2013.01); *G02B 23/2423* (2013.01); *G02B 23/2484* (2013.01)

(58) Field of Classification Search
CPC .......... A61B 1/00188; H04N 5/23212; H04N 5/2254; H04N 2005/2255; H04N 5/2253; H04N 5/2251; H04N 5/2259; H04N 5/23296; H04N 5/2257; G02B 7/04; G02B 23/2476; G02B 21/362; G02B 27/0075; G02B 7/005; G02B 7/282; G03B 13/36; G03B 3/10; G03B 3/04; G03B 13/32
See application file for complete search history.

(56) References Cited

U.S. PATENT DOCUMENTS

| | | | |
|---|---|---|---|
| 4,488,039 A | 12/1984 | Sato et al. | |
| 4,846,155 A | 7/1989 | Kimura | |
| 5,021,888 A * | 6/1991 | Kondou | A61B 1/05 348/76 |
| 5,101,278 A | 3/1992 | Itsumi et al. | |
| 5,307,170 A | 4/1994 | Itsumi et al. | |
| 5,442,167 A | 8/1995 | Cornelius et al. | |
| 5,506,912 A | 4/1996 | Nagasaki et al. | |
| 5,575,757 A | 11/1996 | Kennedy et al. | |
| 5,582,576 A * | 12/1996 | Hori | A61B 1/00096 600/118 |
| 5,582,579 A | 12/1996 | Chism et al. | |
| 5,662,584 A | 9/1997 | Hori et al. | |
| 5,817,014 A | 10/1998 | Hori et al. | |
| 5,838,374 A * | 11/1998 | Kikuchi | H02K 41/0356 348/351 |

(Continued)

*Primary Examiner* — Alexandra L Newton
(74) *Attorney, Agent, or Firm* — Whitmyer IP Group LLC

(57) ABSTRACT

A focusable camera module for an endoscope, including a housing including a lens assembly in a distal end of the housing, a carrier disposed within the housing, the carrier having a distal end with an aperture, an image sensor attached inside the carrier adjacent to the aperture, a flexible circuit attached to an edge of the image sensor, and a motor slideably displacing the carrier between a retracted position and an extended position, the aperture adjacent to the lens assembly in the extended position, and an endoscope including the focusable camera module.

19 Claims, 8 Drawing Sheets

(56) References Cited

U.S. PATENT DOCUMENTS

| | | |
|---|---|---|
| 5,895,350 A | 4/1999 | Hori |
| 6,117,071 A | 9/2000 | Ito et al. |
| RE37,356 E | 9/2001 | Hori et al. |
| 6,478,730 B1 | 11/2002 | Bala et al. |
| 7,273,452 B2 | 9/2007 | Barbato et al. |
| 7,852,371 B2 | 12/2010 | Konstorum et al. |
| 8,305,486 B2 | 11/2012 | Mo et al. |
| 2002/0075393 A1* | 6/2002 | Kim .................... H04N 5/2251 348/335 |
| 2008/0108869 A1* | 5/2008 | Sanders ............. A61B 1/00105 600/109 |
| 2010/0081875 A1* | 4/2010 | Fowler ............... A61B 1/00188 600/114 |
| 2012/0105612 A1* | 5/2012 | Yoshino ............. A61B 1/00009 348/65 |
| 2014/0111628 A1* | 4/2014 | Yoshino ............. H04N 5/23296 348/65 |
| 2014/0210945 A1* | 7/2014 | Morizumi .......... A61B 1/00096 348/45 |
| 2015/0157187 A1* | 6/2015 | Cerveri ............. A61B 1/00188 600/118 |

* cited by examiner

FOCUSABLE CAMERA MODULE FOR ENDOSCOPES

FIELD OF THE INVENTION

The invention relates to endoscope devices, and more specifically to a device and method for focusing endoscope cameras.

BACKGROUND OF THE INVENTION

Video endoscope imager assemblies are generally fixed focus systems in which the distance between the objective lens and the image sensor is fixed. The depth of field achieved is therefore strictly determined by the capability of the objective lens. As such, most endoscopes cannot achieve a focused image at both far and very short distal distances. A typical endoscope will not focus closer than 3 to 5 mm from the distal face.

Further, imager assemblies for endoscopes have lateral size restrictions which places restrictions on focusing mechanisms. While most applications try to reduce the axial height of the imager, endoscopes require imager assemblies that can typically fit into a 5 mm diameter (or smaller) hole.

Some attempts have been made to achieve a focusable camera system using a fixed image sensor with a camera lens that can move axially to adjust the distance between the lens and the image sensor. However, for an endoscope, this is not practical for many reasons. The outside of an endoscope has to be sealed, and the window of the objective lens has to be stationary to achieve this. Also, a typical opto-mechanical system to move a lens assembly is very wide making the camera module much too big to fit into an endoscope.

U.S. Pat. No. 8,305,486 to Mo et al. discloses an auto-focus camera for optical system with a movable sensor for intra-oral use. However, the imager is mounted separate from and distal to the motor, without sufficient supporting structure, and is therefore not adequately secured from unwanted movement or tilting. Mo et al. also does not disclose how to adapt the device being for use in the distal tip of an endoscope, nor does the design appear to be readily scalable to accommodate such applications. Further, Mo et al. concerns auto-focusing only and does not provide a means for manual adjustment by the user.

SUMMARY OF THE INVENTION

Accordingly, it is an object of the present invention to provide a focusable camera module for endoscopes.

These and other objects are achieved by providing a focusable camera module for an endoscope, including a housing including a lens assembly in a distal end of the housing, a carrier disposed within the housing, the carrier having a distal end with an aperture, an image sensor attached inside the carrier adjacent to the aperture, a flexible circuit attached to an edge of the image sensor, and a motor slideably displacing the carrier between a retracted position and an extended position, the aperture adjacent to the lens assembly in the extended position.

In some embodiments, the motor is a piezoelectric motor and/or includes a screw that translates the carrier in a first direction towards the retracted position and a second direction towards the extended position. The screw may act against an interior wall of the carrier at proximal end of the carrier. In some embodiments, the motor is mounted to the housing and the carrier surrounds the motor.

Further provided is an endoscope, including a handle with a control module, a shaft having a distal end, and a camera module provided in the distal end of the shaft. The camera module includes a housing including a lens assembly in a distal end of the housing, a carrier disposed within the housing, the carrier having a distal end with an aperture, an image sensor attached to the carrier adjacent to the aperture, a circuit attached to the image sensor, and a motor slideably displacing the carrier between a retracted position and an extended position, the aperture adjacent to the lens assembly in the extended position.

In some embodiments, the motor is actuated via user input to the control module on an exterior surface of the handle. The control module may include a first control element to allow a user to selectively displace the carrier in a first direction, and a second control element to allow the user to selectively displace the carrier in a second direction, to focus the image sensor.

Also provided is a method of focusing an endoscope, including the steps of receiving a signal to focus an image sensor of the endoscope and actuating a motor to translate a carrier in one of two directions, wherein the carrier surrounds the motor and includes the image sensor mounted therein, translation of the carrier moving the image sensor towards or away from a lens assembly at a distal end of the endoscope.

In some embodiments, the motor is actuated in response to the signal generated in response to user input to a control module on an exterior surface of the endoscope, the control module including a first control element to allow a user to selectively displace the carrier in a first one of the two directions, and a second control element to allow the user to selectively displace the carrier in a second one of the two directions, to focus the image sensor. The step of actuating the motor may include the motor driving a screw which acts against an interior wall of the carrier at a proximal end of the carrier to translate the carrier.

Further provided is a focusable camera module for an endoscope including a housing with a lens assembly in a distal end of the housing, a carrier element disposed within the housing, and an image sensor attached to the carrier element. The module includes a motor slideably displacing the carrier element in a direction towards an extended position, such that the image sensor is adjacent to the lens assembly in the extended position, and a flexible circuit attached to an edge of the image sensor and extending over the carrier element and the motor. The module further includes a spring disposed between the image sensor and the lens assembly, the spring displacing the carrier element in a direction towards a retracted position. Further provided is an endoscope including a shaft having a distal end including such a focusable camera module, and a handle connected to the shaft, the handle including a control module on an exterior surface, wherein the motor is actuated via user input to the control module.

Other objects of the invention and its particular features and advantages will become more apparent from consideration of the following drawings and accompanying detailed description.

DETAILED DESCRIPTION OF THE INVENTION

Figure 1:
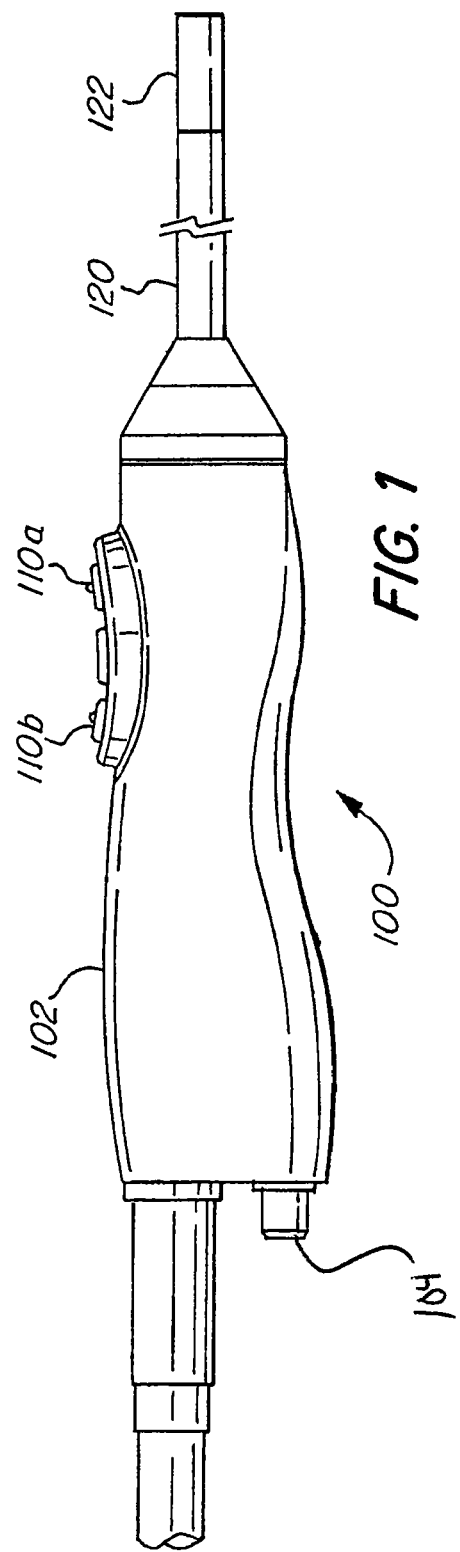
FIG. 1 illustrates an endoscope according to the present invention.

FIG. 1 illustrates an endoscope 100 according to the present invention. The endoscope 100 includes a handle portion 102 and a shaft 120 having a distal end 122. The endoscope 100 may also include a control module 110 includes one or more control elements, such as buttons 110a and 110b. In some embodiments, the endoscope 100 includes a light guide port 104 for connecting an illumination source. In other embodiments, an illumination source in provided within the endoscope 100.

Figure 2:
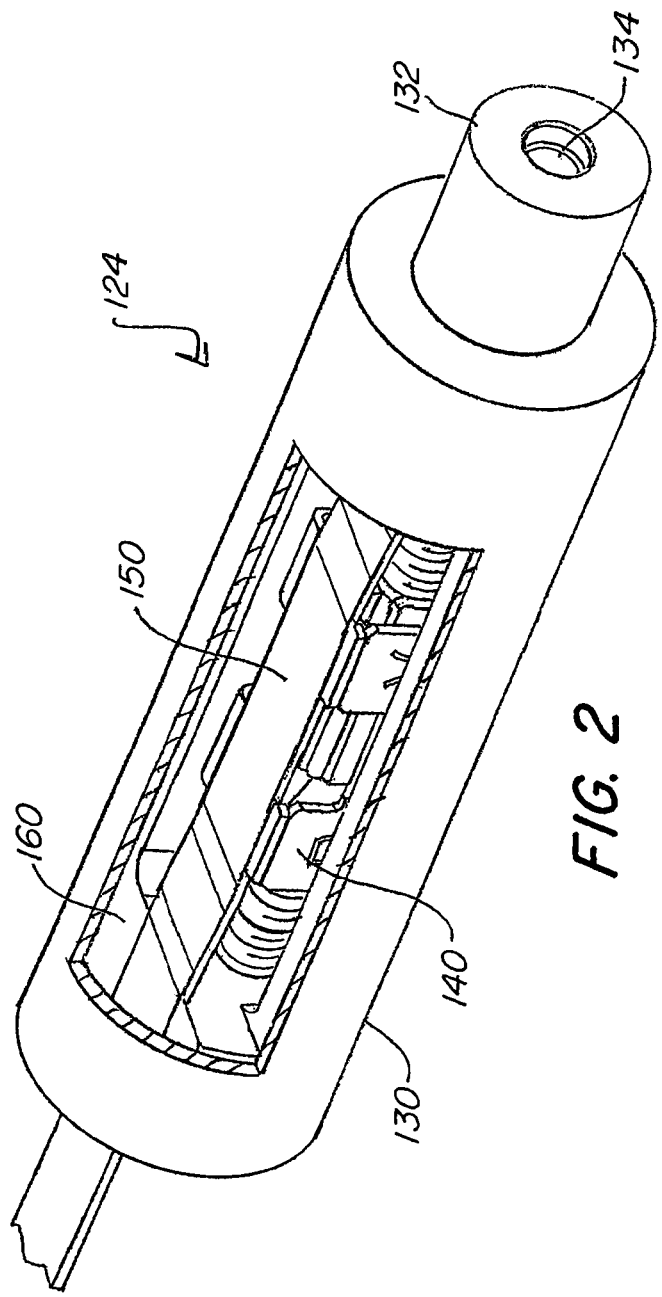
FIG. 2 illustrates a focusable camera module of the endoscope shown in FIG. 1.

The endoscope 100 includes a focusable camera module 124, preferably located within the distal end 122 of the shaft 120. FIG. 2 illustrates an exemplary camera module 124 according to the present invention. The camera module 124 includes a housing 130 (with a section of the exterior wall removed for illustration purposes) having a distal end 132 enclosing a lens assembly 134. As discussed below, the camera module 124 further includes an image sensor 170 adjustable in position with respect to the lens assembly 134. The housing 130 preferably has a diameter of less than 5 mm. Within the housing 130, an elongated carrier 160 is contained which is slideable, forward and backward, within the housing 130. For example, the carrier 160 may be moved forward and backward by means of a motor 140. The control module 110 may be in communication with a driver circuit (e.g., located within the endoscope 100) to transmit signals to the motor 140.

Figure 3:
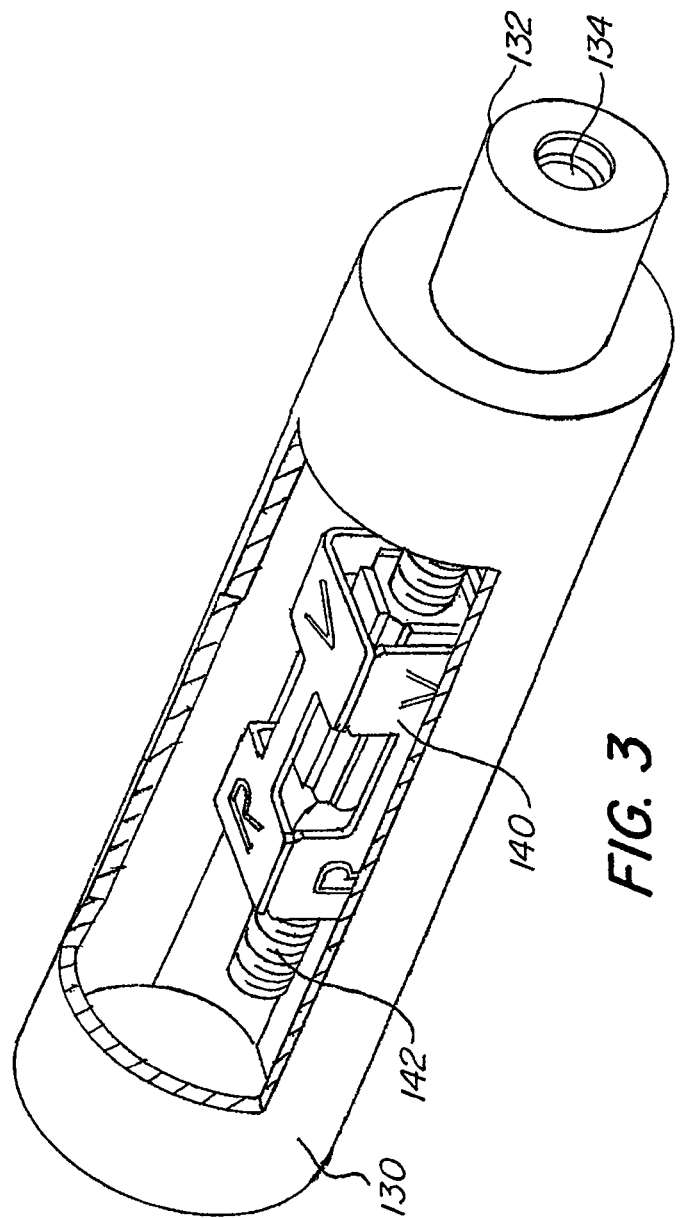
FIG. 3 illustrates a housing and motor of the focusable camera module shown in FIG. 2.

FIG. 3 illustrates the housing 130 with the carrier 160 removed for the purpose of clarity. As shown, the housing 130 includes the motor 140 mounted to, or otherwise fixed in position with respect to, a bottom (e.g., flat) surface of the housing 130. The motor 140 may be, for example, a piezoelectric motor which actuates a screw 142. The motor 140 remains fixed in the housing 130 and acts on the carrier 160 (pushing on either side of the carrier 160 with the screws 142) to move it forward and backward within the housing 130, e.g., towards and away from the lens assembly 134, to focus the image sensor 170.

Figure 4:
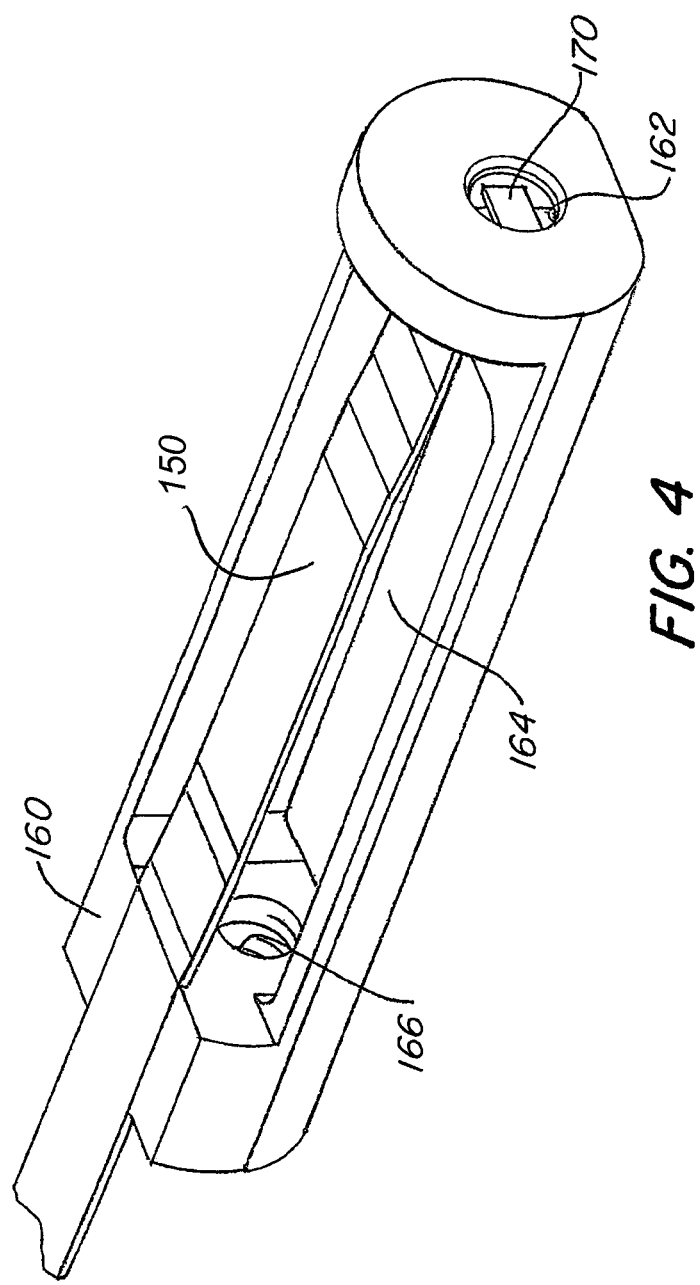
FIG. 4 illustrates a carrier of the focusable camera module shown in FIG. 2.

FIG. 4 further illustrates the carrier 160. The carrier 160 has an elongated shape with sides shaped complementary to interior surfaces of the housing 130, such as curved surfaces. In some embodiments, the carrier 160 further includes a flat bottom surface to compliment a flat bottom surface on the interior of the housing 130. The carrier 160 includes an aperture 162 which, when the carrier 160 is in a forward most position, is adjacent to the lens assembly 134, which is fixed in place in the distal end 132 of the housing 130. The image sensor 170 is mounted in or on the carrier 160 adjacent to or in the aperture 162 (such that the image sensor is at or immediately behind the distal surface of the carrier 160), preferably on an interior side of the carrier 160 and in line with the motor 140. The image sensor 170 may also be mounted on the outside front face of the carrier 160. As such, the image sensor 170 is securely mounted to a slideable assembly, the carrier 160.

The image sensor 170 includes a circuit 150 connected thereto to transmit data from the image sensor 170 via the endoscope. The circuit 150 may be, for example, a flexible circuit which extends over the carrier 160 and/or the motor 140.

The carrier 160 includes an opening 164 to surround the motor 140 fixed to the bottom surface of the housing 130. The carrier 160 also includes an interior wall at a proximal end of the carrier 160, e.g., with a cavity 166 for a screw 142 of the motor 140 to press into (or pull against) to move the carrier 160. The carrier 160 provides stable walls for the motor screw 142 to push on without risk of damaging the image sensor 170. It also provides a long contact surface with the housing 130 to prevent the image sensor 170 from tilting during movement and provide an accurate and stable forward and backward movement.

Figure 5:
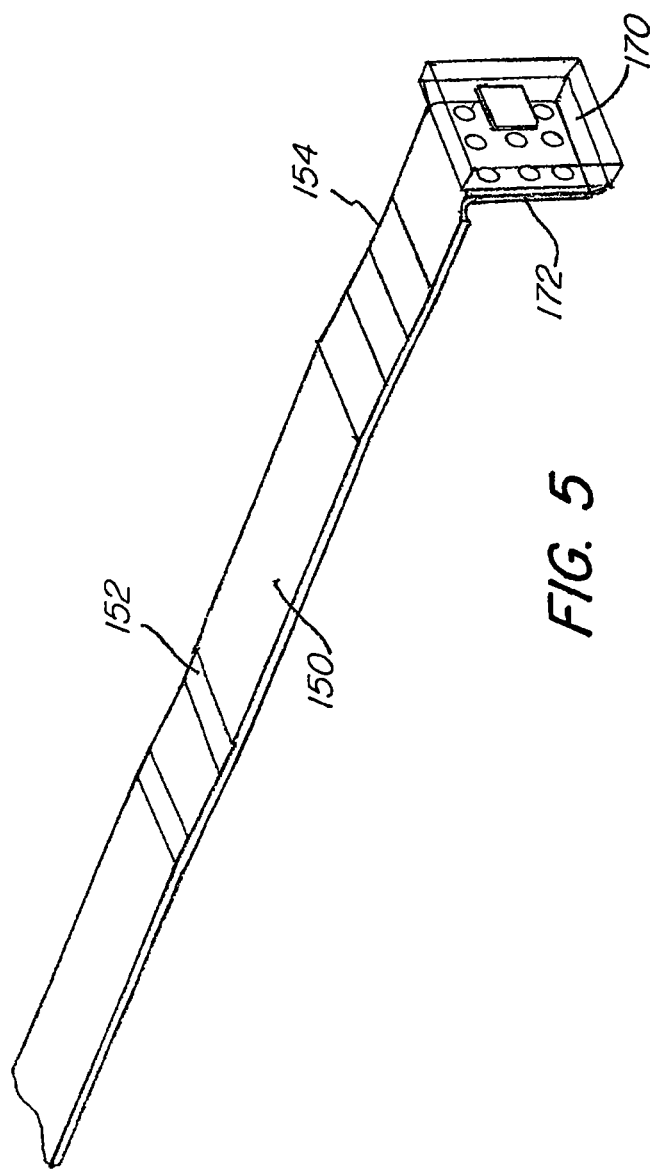
FIG. 5 illustrates an image sensor and circuit of the focusable camera module shown in FIG. 2.

FIG. 5 further illustrates the image sensor 170 and the flexible circuit 150. The image sensor 170 may be, for example, a charge-coupled device (CCD) or a complementary metal-oxide-semiconductor (CMOS). The image sensor 170 may include a ball grid array (BGA) 172 on the back of the image sensor 170. The flexible circuit 150 may be attached to the BGA 172 on the back of the image sensor 170, at a top portion, and is then bent at an angle, such as ninety (90) degrees, to extend over and above the motor 140. In some embodiments, the circuit 150 includes fold regions or lines 152 or 154 to assist when the circuit is compressed by the movement of the carrier 160. The flexible nature of the circuit 150 allows the circuit 150 to extend and retract with the movement of the carrier 160.

The use of the flexible circuit 150, and particularly its connection to a top edge of the image sensor 170, allows for a space reduction not achieved in prior art designs. This configuration further allows the motor 140 to be place directly behind the image sensor 170 which is generally not possible when an image sensor has a cable exiting out of the back center of the image sensor.

Figure 6:
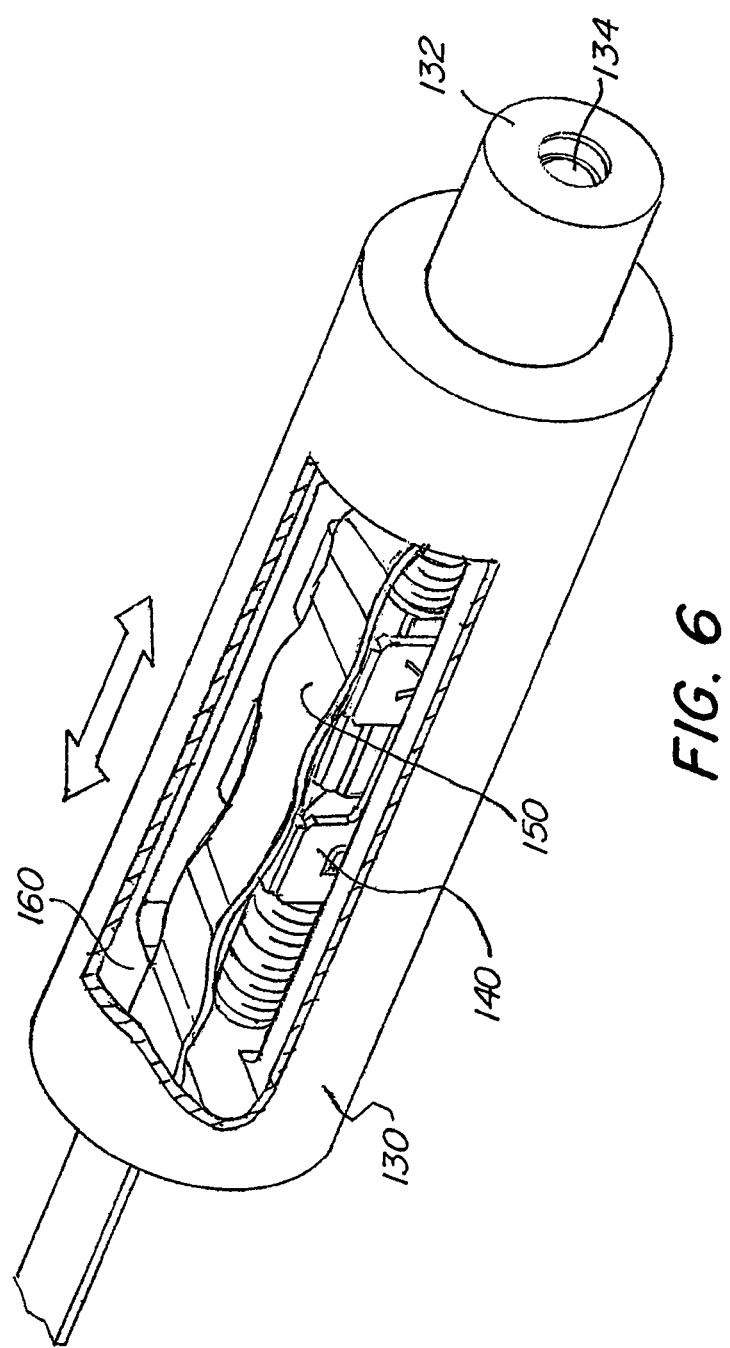
FIG. 6 illustrates a focusable camera module of the endoscope shown in FIG. 1.

As shown in FIG. 6, the carrier 160 can be moved forward and backward within the housing 130 to adjust the position of the image sensor 170, or focal distance, with respect to the lens assembly 134. In particular, the carrier 160 may be moved and, in turn, the focal distance may be adjusted, by a user of the endoscope using the control elements 110a and 110b. The control elements 110a and 110b transmit signals to the motor 140, e.g., via a driver circuit, to actuate the motor 140 which acts on the carrier 160. By enabling the image sensor 170 to be moved, the image sensor 170 is able to focus at distal distances less than 1 mm.

In some embodiments, the carrier 160 may be actuated and selectively positioned by the user at any location along a range of movement of the carrier 160, e.g., by holding and releasing one of the control elements 110a/110b. In some embodiments, the carrier 160 may be selectively positioned at discrete steps along the range of movement by the user, e.g., by pressing one of the control elements 110a/110b to advance to the next step. For example, several discrete steps could be preconfigured by the manufacturer for ease of use, such as normal, close, and very close. In some embodiments, the device is configured to auto focus using the motor 140 without the user having to actuate the control elements 110a/110b. An auto-focus setup may be achieved with a drive control loop to automatically adjust the back focus distance to always achieve focus at any distal distance.

The focusable camera module 124 and endoscope 100 described herein may be used in a performing a method of focusing an endoscope. The method may include the steps of receiving a signal to focus the image sensor 170 of the endoscope 100 and actuating the motor 140 to translate the carrier 160 in one of two directions, wherein the carrier 160 surrounds the motor 140 and includes the image sensor 170 mounted therein, translation of the carrier 160 moving the image sensor 170 towards or away from a lens assembly 134 at a distal end of the endoscope 100.

Figure 7:
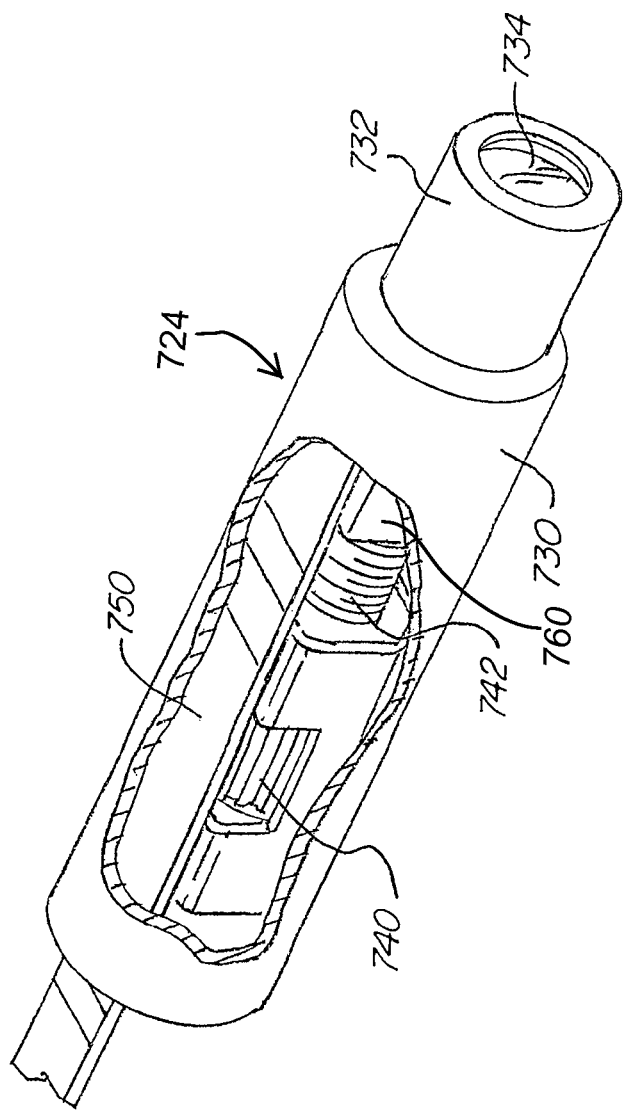
FIG. 7 illustrates a focusable camera module of the endoscope shown in FIG. 1.
Figure 8:
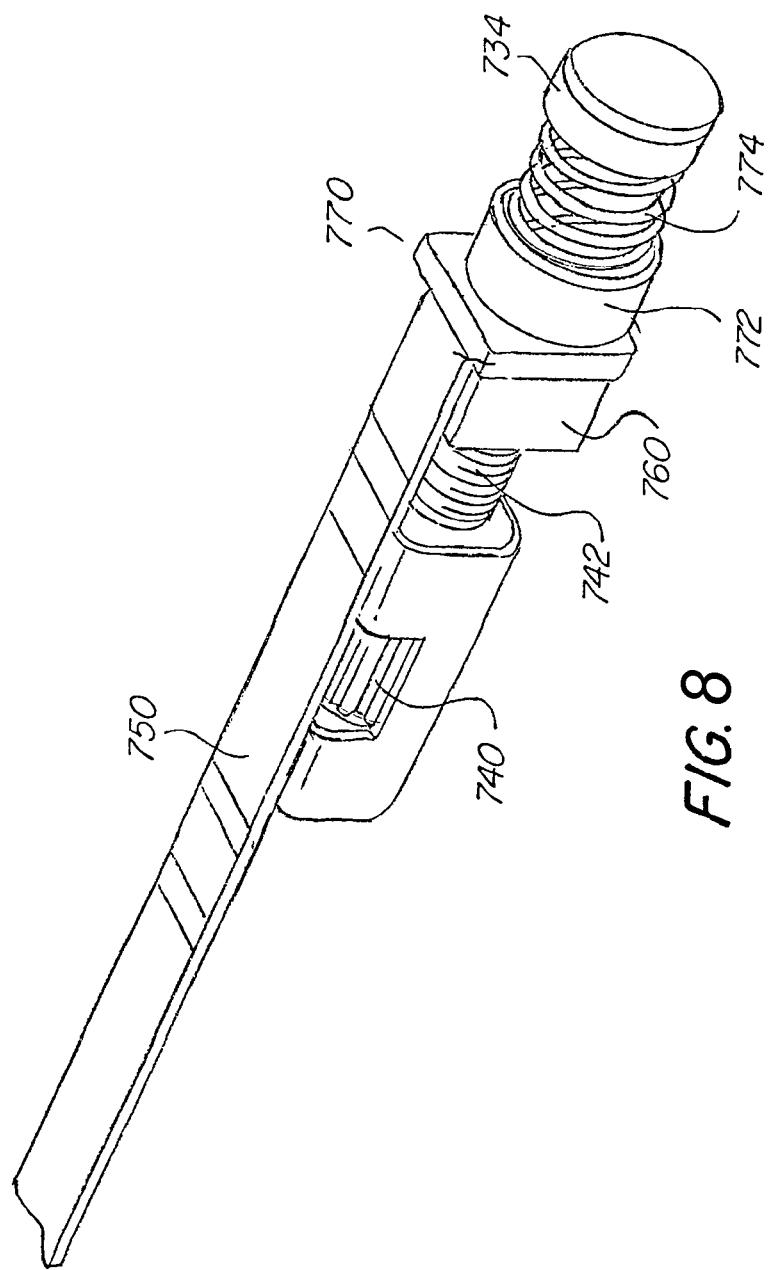
FIG. 8 illustrates components of the focusable camera module shown in FIG. 7.

FIGS. 7-8 illustrate another camera module 724 according to the present invention. The camera module 724 includes a housing 730 (with a section of the exterior wall removed for illustration purposes) having a distal end 732 enclosing a lens assembly 734. The housing 730 preferably has a diameter of less than 5 mm, or less than 4 mm. The camera module 724 further includes an image sensor 770 adjustable in position with respect to the lens assembly 734.

A motor 740 is mounted to, or otherwise fixed in position with respect to, a bottom (e.g., flat) surface of the housing 730. The motor 740 may be, for example, a piezoelectric motor which actuates a screw 742 on a forward end of the motor 740.

In the present embodiment, the elongated carrier is replaced with a small carrier element or plate 760 on only one (forward) side of the motor 740. Without an elongated carrier around the sides of the motor 740, the diameter of the housing 730 may be further reduced. Further, the length of the module may also be reduced. While the carrier element 760 is shown to be thicker than the image sensor in FIG. 8, it can be any thickness (e.g., less than the image sensor 770) sufficient to accommodate the end of the screw 742.

The motor 740 remains fixed in the housing 730 and acts on the carrier element 760 to move it forward within the housing 730, e.g., towards the lens assembly 734, to focus the image sensor 770. To move the image carrier element 760 and image sensor 770 in the rearward direction, the camera module 724 includes a spring 774 between the image sensor 770 and the lens assembly 734. In some embodiments, the camera module 724 includes a spring coupling 772 between the spring 774 and the image sensor 770. When the motor 740 is actuated in a rearward direction, the image sensor 770 is moved rearward by action of the spring 774 rather than a pulling or pushing force of the motor 740.

The image sensor 770 includes a flexible circuit 750 connected thereto to transmit data from the image sensor 770 via the endoscope. The flexible circuit 750 extends over the carrier element 760 and the motor 740. The flexible circuit 750 may be attached to the back of the image sensor 770 (or a BGA thereof) at a top portion, and is then bent at an angle, such as ninety (90) degrees, to extend over and above the motor 740, thus freeing space behind the image sensor 770. The placement of the image sensor, motor, and flexible circuit, and the connection of the flexible circuit, in this and the other embodiments described herein, minimize space which is desired for endoscope camera modules.

Although the invention has been described with reference to a particular arrangement of parts, features and the like, these are not intended to exhaust all possible arrangements or features, and indeed many modifications and variations will be ascertainable to those of skill in the art.

What is claimed is:

1. A focusable camera module for positioning entirely within a distal end of a shaft of an endoscope, the focusable camera module comprising:
   a housing including a lens assembly fixed in place in a distal end of said housing;
   a carrier disposed within said housing, said carrier having a distal end with an aperture;
   an image sensor attached inside said carrier adjacent to the aperture;
   a flexible circuit attached to an edge of said image sensor; and
   a piezoelectric motor mounted to and fixed in place relative to the housing, the motor slideably displacing the carrier relative to the housing between a retracted position and an extended position, the aperture adjacent to the lens assembly in the extended position;
   wherein the motor includes a screw that translates the carrier in a first direction towards the retracted position and a second direction towards the extended position.

2. The camera module according to claim 1, wherein the screw acts against an interior wall of said carrier at proximal end of said carrier.

3. The camera module according to claim 1, wherein said carrier is selectively positionable at a plurality of positions between the retracted position and the extended position.

4. The camera module according to claim 1, wherein said motor is positioned axially behind the image sensor and towards the retracted position.

5. The camera module according to claim 1, wherein the flexible circuit is attached to a top edge of said image sensor and substantially perpendicular to said image sensor.

6. The camera module according to claim 1, wherein said image sensor is one of a charge-coupled device (CCD) or a complementary metal-oxide-semiconductor (CMOS).

7. The camera module according to claim 1, wherein said carrier has an exterior surface with a shape complementary to an interior surface of said housing.

8. An endoscope, comprising:
   a shaft having a distal end;
   a focusable camera module positioned entirely within the distal end of said shaft, the focusable camera module including:
      a housing including a lens assembly fixed in place in a distal end of said housing;
      a carrier disposed within said housing, said carrier having a distal end with an aperture;
      an image sensor attached inside said carrier adjacent to the aperture;
      a flexible circuit attached to an edge of said image sensor; and
      a piezoelectric motor mounted to and fixed in place relative to the housing, the motor slideably displacing the carrier relative to the housing between a retracted position and an extended position, the aperture adjacent to the lens assembly in the extended position;
      wherein the motor includes a screw that translates said carrier in a first direction towards the retracted position and a second direction towards the extended position; and
   a handle connected to said shaft, said handle including a control module on an exterior surface of said handle, wherein said motor is actuated via user input to the control module.

9. The endoscope according to claim 8, wherein the screw acts against an interior wall of said carrier at proximal end of said carrier.

10. The endoscope according to claim 8, wherein the control module includes a first control element to allow a user to selectively displace the carrier in a first direction, and a second control element to allow the user to selectively displace the carrier in a second direction, to focus the image sensor.

11. The endoscope according to claim 10, wherein said carrier is selectively positionable by the user at a plurality of positions between the retracted position and the extended position.

12. The camera module according to claim 1, wherein said carrier is positionable at a plurality of positions between the retracted position and the extended position.

13. The camera module according to claim 1, wherein the motor is entirely within the housing.

14. The camera module according to claim 1, wherein the lens assembly is an objective lens assembly at the distal end of the housing.

15. The camera module according to claim 1, wherein the flexible circuit includes a fold area within the housing at which the flexible circuit folds when compressed by movement of the carrier from the extended position to the retracted position.

16. The camera module according to claim 1, wherein the flexible circuit extends and retracts with movement of the carrier relative to the housing between the extended position and the retracted position.

17. The camera module according to claim 1, wherein an image of an object formed by the lens assembly coincides with an image plane of the image sensor when the object is at a distance of 1 mm or less from a distal face of the lens assembly.

18. The camera module according to claim 1, wherein the housing has a maximum width defined in a direction perpendicular to a direction in which the motor slidably displaces the carrier; and wherein the maximum width of the housing is less than 5 mm.

19. The camera module according to claim 1, wherein the motor and the image sensor are discrete components positioned at a distance relative to one another.

* * * * *